United States Patent [19]
Schulz

[11] 3,964,468
[45] June 22, 1976

[54] BIOPTOME

[75] Inventor: Werner P. Schulz, San Bruno, Calif.

[73] Assignee: The Board of Trustees of Leland Stanford Junior University, Stanford, Conn.

[22] Filed: May 30, 1975

[21] Appl. No.: 582,210

[52] U.S. Cl. ............................. 128/2 B; 128/305; 128/321
[51] Int. Cl.² ..................... A61B 5/00; A61B 17/32; A61B 17/28
[58] Field of Search ..................... 128/2 B, 305, 321

[56] References Cited
UNITED STATES PATENTS

| | | | |
|---|---|---|---|
| 2,113,246 | 4/1938 | Wappler | 128/321 |
| 2,790,437 | 4/1957 | Moore | 128/2 B |
| 3,796,211 | 3/1974 | Kohl | 128/2 B |
| 3,895,636 | 7/1975 | Schmidt | 128/321 X |

FOREIGN PATENTS OR APPLICATIONS

| | | | |
|---|---|---|---|
| 1,069,398 | 5/1967 | United Kingdom | 128/2 B |

*Primary Examiner*—Channing L. Pace
*Attorney, Agent, or Firm*—Thomas E. Ciotti

[57] ABSTRACT

Three improvements to a prior art bioptome are disclosed. The prior art bioptome comprises: tongs, an elongated flexible spiral wire catheter attached to the working end of one of the legs of the tongs; an elongated wire that is rotationally jointed to the working end of the other leg of the tongs and extends axially through the catheter; seals between the inner surface of the catheter and the wire at both ends of the catheter; a pair of hinged jaws one of which is fixed and attached to the end of the catheter and the other of which is movable and is attached to the end of the wire; and a heat-shrunk plastic sleeve about the catheter that seals the radial exterior surface of the catheter and prevents the catheter from substantial axial expansion. The basic improvement is a heat-shrunk plastic inner sleeve about a segment of the catheter that together with the main sleeve forms a double sleeve about said segment, the inner sleeve having an end that is bias-cut. A further improvement comprises screw fitting the seals between the catheter and wire whereby they are compressed and form a tighter seal against fluid flow into or out of the catheter bore. A still further improvement is a rigid support and guide tube attached to the rotaional joint and extending axially about the elongated wire between the working ends of the tongs.

6 Claims, 4 Drawing Figures

BIOPTOME

BACKGROUND OF THE INVENTION

1. Field of the Invention

This invention relates to a bioptome for making extractions from within the body.

2. Description of the Prior Art

A bioptome is a medical instrument that is used to make extractions, usually of biopsy tissue specimens, from within the body. It basically consists of three parts: an elongated member that may be inserted into the body to the extraction site via body canals such as the circulatory system, the urinary tract or the respiratory system, a pair of jaws attached to one end of the elongated member, and a handle attached to the other end of the elongated member by which the jaws are operated remotely.

The bioptome of the present invention began as an almost complete modification of a bioptome developed in Japan by Konno and Sakakibara and described in *Japan Heart J*, v 3, pp 537– 42, 1962. That modification and several versions of it have been in use at Stanford University for several years and have been on sale in the United States prior to May 1974. Those bioptomes were designed, manufactured and sold by the inventor of the present invention and are described in "Experience with Fifty-four Cardiac Transplants", *Surgery*, v 74, 1973 and "A New Instrument for Transvenous Cardiac Biopsy", *Amer J of Cardiology*, v 33, February 1974. The present invention is an improved version of those bioptomes.

SUMMARY OF THE INVENTION

The bioptome that has been improved upon according to the invention comprises: tongs; a rotational joint socket mounted on the working end of one of the legs of the tongs; a rigid tubular barrel mounted at one of its ends to the working end of the other leg of the tongs; an elongated flexible spiral wire catheter attached at one of its ends to the other end of said barrel; an elongated center wire that extends axially through the bores of said barrel and said catheter and has a joint on its one end that is received in said socket; a seal between the center wire and the catheter at each end of the catheter; a pair of hinged jaws one of which is mounted on the other end of the catheter and the other of which is attached to the other end of the center wire; and a heat-shrunk plastic sleeve about the catheter that seals the radial exterior surface of the catheter and prevents the catheter from substantial axial expansion.

The basic improvement on the above described bioptome comprises a heat-shrunk plastic inner sleeve about the barrel and a segment of the catheter that together with the main sleeve forms a double sleeve about the barrel and said segment, the inner sleeve having an end that is about the segment that is bias-cut. The inner sleeve provides additional axial rigidity at and adjacent the barrel-catheter junction and the bias-cut end of the inner sleeve distributes the stress at the double sleeve-single sleeve transition in a progressively decreasing manner thereby preventing failure and breakage at that point.

A further improvement of the above described bioptome comprises screw fitting the seals between the catheter and center wire whereby they are compressed and form a tighter seal against fluid flow into or out of the catheter bore. Such sealing prevents fluid from within the catheter from contaminating the body and also prevents body fluids from entering the catheter bore and hindering subsequent cleaning and sterilization of the bioptome.

A third improvement is a rigid center wire guide and support tube, one end of which is attached to said joint, that extends axially about the center wire from said joint into the bore of said barrel. The guide and support tube prevents the center wire from buckling without affecting its general flexibility.

DETAILED DESCRIPTION OF THE INVENTION

Figure 1:
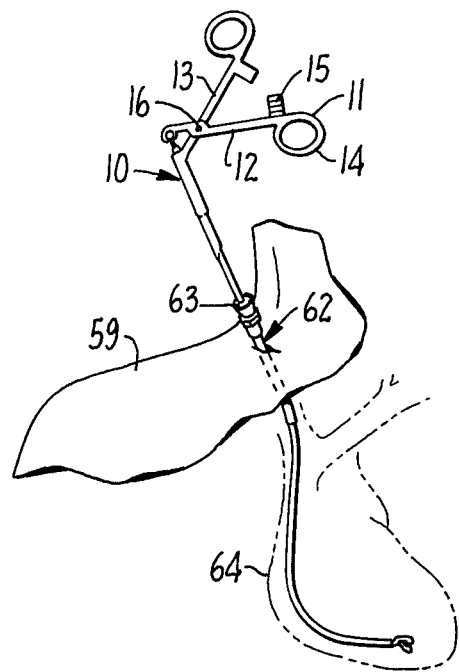
FIG. 1 is a reduced illustration of the bioptome being used to obtain an endomyocardial biopsy specimen from the apex of the right ventricle of a human heart.
Figure 3:
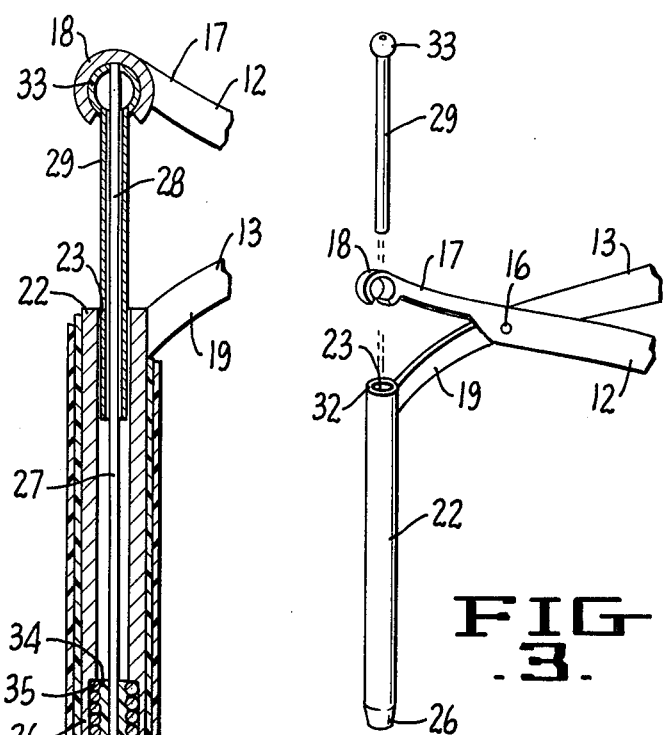
FIG. 3 is an exploded view of the portion of the bioptome shown in FIG. 2.
Figure 2:
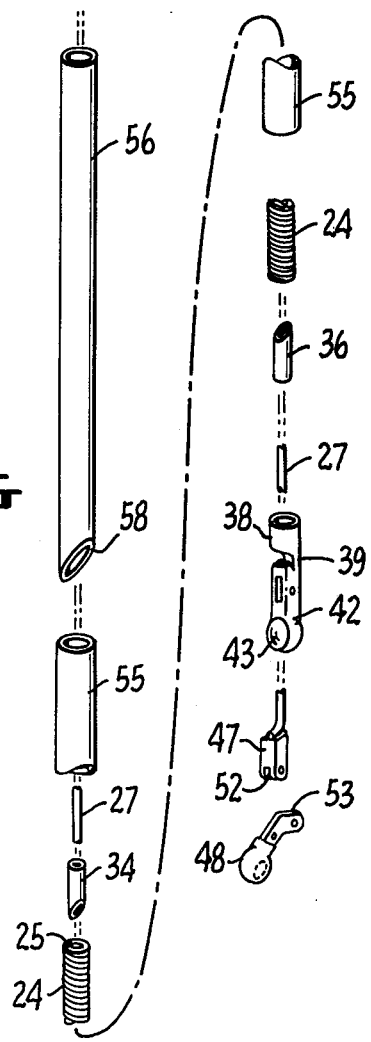
FIG. 2 is an enlarged, elevational, sectional view of a portion of the bioptome of FIG. 1.

The bioptome of the invention, generally designated 10 in the drawings, is an integral instrument. The part of bioptome 10 that is manipulated directly by the doctor is tongs 11 (FIG. 1). Tongs 11 comprise a pair of legs 12, 13 that are hinged by a pin at 16. Each of legs 12, 13 has a finger grip 14 and a ratchet bar 15. Working end 17 of leg 12 terminates in a joint socket 18 (FIGS. 2 and 3). Socket 18 may be either a cylindrical socket or a ball socket. A ball socket is preferred since it provides greater rotational freedom. An elongated tubular barrel 22 is mounted at one of its ends on working end 19 of leg 13 in the plane of movement of legs 12, 13 with the opening of its center bore 23 facing socket 18.

One end of a flexible catheter 24 formed of tightly spiralled 20 mil (approx. 0.5 mm) D wire and having an 80 mil (approx 2 mm) OD and a 40 mil (approx 1 mm) D center bore 25 is soldered into end 26 of barrel 22. As seen in FIG. 2, a center wire 27, 20 mil (approx 0.5 mm) D, extends axially through bores 23, 25 of barrel 22 and catheter 24 respectively. One end, designated 28, of center wire 27 extends into and through a guide tube 29. One end of guide tube 29 fits into bore 23 of barrel 22 and the other end terminates in a ball 33 that sits in socket 18 and freely rotates therein. End 28 of wire 27 is soldered within ball 33. A tubular polytetrafluoroethylene (sold under the trademark TEFLON) seal 34 is screwed into end 35 of catheter 24 about the center wire 27. The inner end of seal 34 is bias-cut, preferably about 20° to 40° relative to the longitudinal axis of the sleeve, to make the insertion of seal 34 easier. Thus, seal 34 is compressed and seals end 35 against fluid flow into or out of bore 25, but still permits axial movement of wire 27 within catheter 24. An identical seal 36 seals the other end 37 of catheter 24. The remaining space within bore 25 not occupied by wire 27 is filled with silicone lubricant.

Figure 4:
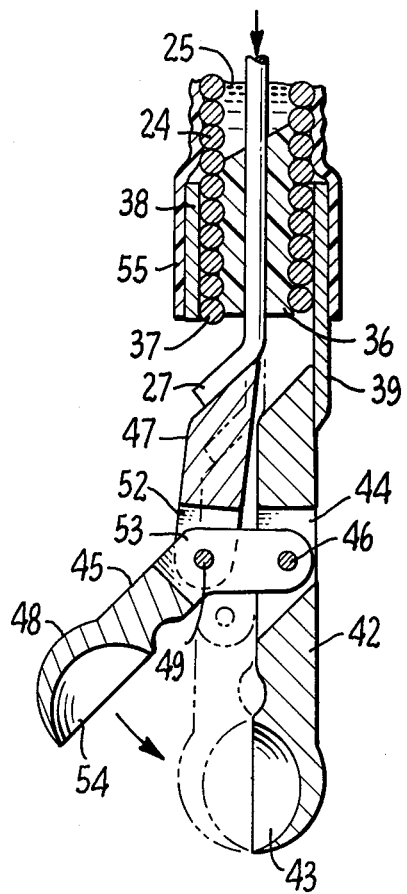
FIG. 4 is an enlarged, elevational, sectional view of the jaws of the bioptome of FIG. 1.

Referring to FIG. 4, a generally cylindrical jaw support member 38 is attached about end 37 of catheter 24. A lower portion 39 of member 38 extends axially outwardly from end 37 of catheter 24 and provides an attachment site for a lower jaw 42. As indicated in FIG. 4, lower jaw 42 is stationary. Lower jaw 42 has a generally semispherical cup 43 in its leading end that is defined by a sharp cutting edge. Jaw 42 also has a slot 44 in which an upper jaw 45 is hinged by a pin 46. Upper jaw 45 consists of a rear member 47 and a front member 48 that are hinged together by a pin 49. One end of rear member 47 is attached to the leading end of center wire 27 and the other end of member 47 has a way 52 in it that receives an elbow 53 of front member 48. Pin 49 runs through elbow 53. The leading end of member 48 is provided with a semispherical cup 54 that is defined by a sharp cutting edge. As illustrated in phantom in FIG. 4, cups 43, 54 register when jaws 42, 45 are closed and together form a generally spherical recess.

The radial exterior surface of catheter 24 is hermetically sealed with a heat-shrunk plastic sleeve 55 made from irradiated polyvinylidene fluoride (sold under the trademark KYNAR by Raychem Corp). In addition to sealing the exterior of catheter 24, sleeve 55 also provides axial rigidity and prevents catheter 24 from expanding axially. Such expansion would adversely affect the operation of jaws 42, 45. An inner heat-shrunk sleeve 56 made from the same material as sleeve 55 provides additional rigidity at and adjacent to the junction of barrel 22 and catheter 24. As depicted in FIG. 2, sleeves 55 and 56 together form a double sleeve about barrel 22 and a segment of catheter 24 immediately adjacent said junction. The point, designated 57, at which sleeve 56 ends and sleeve 55 continues about catheter 24 was found to be particularly susceptible to stress failure and breakage. In accordance with this invention it was further found that such susceptibility could be reduced significantly by making end 58 of sleeve 56 bias-cut, preferably downwardly toward barrel 22 at 20° to 40° from horizontal.

All of the parts of bioptome 10, with the exception of seals 34, 36 and sleeves 55, 56, may be made from stainless steel. The various mountings and attachments of the parts may be made by soldering or brazing, as is appropriate.

The operation of bioptome 10 is very simple. As the tongs 11 are opened, working ends 17, 19 of arms 12, 13 are spread apart causing center wire 27 to be pulled in the direction of movement of arm 12 (toward the right or top of FIG. 2). Rear member 47, being attached to center wire 27, is also pulled in that direction. Since jaw 42 is fixed, member 48 pivots upwardly and rearwardly about pins 46, 49 into its open position as shown in solid lines in FIG. 4. Closing of tongs 11 draws ends 17, 19 toward each other and pushes center wire 27 in the opposite direction (illustrated by the straight arrow in FIG. 4). Such closing pivots upper jaw 45 forwardly and downwardly (illustrated by the curved arrow in FIG. 4) into its closed position (shown in phantom in FIG. 2 and in solid in FIG. 3) clenched against lower jaw 42. Jaws 42, 45 may be locked reversibly in their clenched position by interengaging ratchet bars 15 of tongs 11.

The use of the bioptome to obtain a tissue sample is also simple. It may be used to obtain tissue samples from the ventricles of the human heart by the procedure described in "A New Instrument for Transvenous Biopsy", *Amer J Cardiology*, v 33, p 264, Feb. 1974. Referring to FIG. 1 the procedure is described briefly below. Under local anesthesia a cannula is inserted into the jugular vein through an incision at the base of the neck of a patient 59. A flexible guidewire is then inserted through the cannula and a false catheter and sheath, generally designated 62, are passed over the guidewire into the vein. The catheter 24 is introduced into the vein through sheath 62 with the jaws 42, 45 in their closed position to facilitate passage through the catheter. It is noted that the diameters of the closed jaws and catheter are such as to permit passage through a No. 9F Desilets-Hoffman sheath. A rubber plug 63 that fits about catheter 24 is inserted into a Luerlok fitting at the end of sheath 62 to prevent blood leakage and/or air intake. Catheter 24 is then advanced to the apex of ventricle 64 under fluoroscopic control. The jaws 42, 45 are then opened in the manner described above and pressed against the endomyocardium. The jaws 42, 45 are then closed by closing tongs 11 and interengaging ratchet bars 15. The catheter is then withdrawn steadily, with a small jerk occurring as the specimen caught in the jaws' cups is removed from the endomyocardium. After the catheter 24 is completely withdrawn, sheath 62 is removed and the incision is closed.

Although the above description is related to a bioptome that is designed specifically for obtaining tissue specimens from the heart, the instrument may be readily modified, such as by modifying the size and shape of jaws 42, 45, to adapt it for obtaining tissue from other organs or body sites or for removing natural or foreign objects from within the body, such as kidney stones. Such modifications, as well as others that are obvious to those of skill in the medical instrument art, are intended to be within the scope of the following claims.

I claim:

1. In a bioptome comprising: tongs; a rotational joint socket mounted on the working end of one of the legs of the tongs; a rigid tubular barrel mounted at one of its ends to the working end of the other leg of the tongs; an elongated flexible spiral wire catheter attached at one of its ends to the other end of said barrel; an elongated center wire that extends axially through the bores of said barrel and said catheter and has a joint on its one end that is received in said socket; a seal between the center wire and the catheter at each end of the catheter; a pair of hinged jaws one of which is mounted on the other end of the catheter and the other of which is attached to the other end of the center wire; and a heat-shrunk plastic sleeve about the catheter that seals the radial exterior surface of the catheter and prevents the catheter from substantial axial expansion, the improvement comprising: a heat-shrunk plastic inner sleeve about the barrel and a segment of the catheter that together with said sleeve forms a double sleeve about said barrel and said segment, the end of the inner sleeve that is about the segment being bias-cut.

2. The improvement of claim 1 including the further improvement wherein said seals are screw fitted between the catheter and the center wire whereby they are compressed.

3. The improvement of claim 1 wherein said end of the inner sleeve is biased downwardly toward the barrel.

4. The improvement of claim 1 wherein the bias is about 20°–40° relative to the longitudinal axis of the sleeve.

5. The improvement of claim 1 including the further improvement of a rigid center wire guide and support tube one end of which is attached to said joint that extends axially about the center wire from said joint into the bore of said barrel.

6. The improvement of claim 2 including the still further improvement of a rigid center wire guide and support tube one end of which is attached to said joint that extends axially about the center wire from said joint into the bore of said barrel.

* * * * *

UNITED STATES PATENT OFFICE
CERTIFICATE OF CORRECTION

Patent No. 3,964,468      Dated June 22, 1976

Inventor(s) Werner P. Schulz

It is certified that error appears in the above-identified patent and that said Letters Patent are hereby corrected as shown below:

On the Title Page, Item [73], "Stanford, Conn." should read ---Stanford, Calif.---.

Signed and Sealed this

Fourteenth Day of September 1976

[SEAL]

Attest:

RUTH C. MASON
*Attesting Officer*

C. MARSHALL DANN
*Commissioner of Patents and Trademarks*